(12) United States Patent
Rubin

(10) Patent No.: US 12,290,493 B2
(45) Date of Patent: *May 6, 2025

(54) MORE POTENT AND LESS TOXIC FORMULATIONS OF EPINEPHRINE AND METHODS OF MEDICAL USE

(71) Applicant: Advanced Respiratory Technologies, Inc., Largo, FL (US)

(72) Inventor: Darren Rubin, Largo, FL (US)

(73) Assignee: Advanced Respiratory Technologies, Inc., Largo, FL (US)

( * ) Notice: Subject to any disclaimer, the term of this patent is extended or adjusted under 35 U.S.C. 154(b) by 408 days.

This patent is subject to a terminal disclaimer.

(21) Appl. No.: 17/666,324

(22) Filed: Feb. 7, 2022

(65) Prior Publication Data
US 2022/0151956 A1    May 19, 2022

Related U.S. Application Data

(63) Continuation of application No. 15/991,501, filed on May 29, 2018, now Pat. No. 11,266,611, which is a continuation of application No. 15/616,157, filed on Jun. 7, 2017, now Pat. No. 10,039,728, which is a continuation-in-part of application No. 15/596,440, filed on May 16, 2017, now Pat. No. 10,004,700.

(51) Int. Cl.
| | | |
|---|---|---|
| *A61K 31/137* | (2006.01) |
| *A61K 9/00* | (2006.01) |
| *A61K 45/06* | (2006.01) |
| *A61K 47/02* | (2006.01) |
| *A61K 47/26* | (2006.01) |
| *A61P 7/04* | (2006.01) |
| *A61P 9/02* | (2006.01) |
| *A61P 41/00* | (2006.01) |

(52) U.S. Cl.
CPC ............ *A61K 31/137* (2013.01); *A61K 47/26* (2013.01); *A61P 7/04* (2018.01); *A61P 9/02* (2018.01); *A61P 41/00* (2018.01); *A61K 9/0019* (2013.01); *A61K 9/0085* (2013.01); *A61K 45/06* (2013.01); *A61K 47/02* (2013.01); *A61K 2300/00* (2013.01)

(58) Field of Classification Search
CPC .... A61K 31/137; A61K 47/26; A61K 9/0019; A61P 7/04; A61P 9/02; A61P 41/00
See application file for complete search history.

(56) References Cited

U.S. PATENT DOCUMENTS 9,283,197 B1 * 3/2016 Taneja ................ A61K 31/137

* cited by examiner

*Primary Examiner* — Sahar Javanmard
(74) *Attorney, Agent, or Firm* — Wood, Phillips, Katz, Clark & Mortimer

(57) ABSTRACT

The present invention provides pharmaceutical formulations of levorotatory-epinephrine, l-epinephrine, more potent and less toxic than existing pharmaceutical formulations of epinephrine, along with methods of producing and using these pharmaceutical formulations of l-epinephrine, including preventing and or treating hypotension and hemostasis under surgical anesthesia.

11 Claims, No Drawings

MORE POTENT AND LESS TOXIC FORMULATIONS OF EPINEPHRINE AND METHODS OF MEDICAL USE

CROSS-REFERENCE TO RELATED APPLICATIONS

This application is continuation of U.S. Ser. No. 15/991,501, filed May 29, 2018, which is a continuation-in-part of U.S. Ser. No. 15/616,157, filed Jun. 7, 2017, which is a continuation-in-part of U.S. Ser. No. 15/596,440, filed May 16, 2017, the disclosures of which are hereby incorporated by reference in their entirety.

FEDERALLY SPONSORED RESEARCH OR DEVELOPMENT

Not Applicable.

MICROFICHE/COPYRIGHT REFERENCE

Not Applicable.

FIELD OF THE INVENTION

The present invention provides pharmaceutical formulations of levorotatory-epinephrine, l-epinephrine, more potent and less toxic than existing pharmaceutical formulations of epinephrine, along with methods of producing and using these pharmaceutical formulations of l-epinephrine, including preventing and or treating hypotension and hemostasis under surgical anesthesia.

BACKGROUND OF THE INVENTION

Epinephrine has a long history of pharmaceutical use that spans many decades since this catecholamine was first chemically synthesized at the turn of the twentieth century. Epinephrine is a sympathomimetic drug that acts on both alpha and beta adrenergic receptors found ubiquitously throughout much of the body. Epinephrine has profound effects on the cardiovascular system. Epinephrine has direct myocardial stimulation that increases the strength of ventricular contraction and cardiac output, positive inotropic action; increases heart rate, positive chronotropic action; and causes vasoconstriction in the veins and many vascular beds, positive vasopressor action. Epinephrine remains the first-line inotrope/vasopressor in many parts of the world and is recognized by the World Health Organization as an essential medicine with many medical uses and forms of administration.

As eye drops, epinephrine provides mydriasis, the dilation of the pupil, during intraocular surgery. As a solution for nebulization, epinephrine provides bronchodilation and relief of bronchospasm to asthmatics and those with chronic obstructive pulmonary disease. As a solution combined with analgesics for injection, including lidocaine for dental applications and bupivacaine for epidural analgesia, epinephrine improves and lengthens pain relief and sensory blockade during surgical procedures. Yet, epinephrine has many life saving uses in emergency room settings. As a solution for intramuscular or subcutaneous injection, epinephrine helps alleviate vasodilation, loss of intravascular fluid volume, hypotension, bronchospasm, and other symptoms associated with anaphylaxis, severe allergic reactions. Injections of epinephrine can also help stop bleeding, such as bleeding associated with peptic ulcers and surgical procedures. As a solution for intravenous injection, epinephrine is used as a critical adjunct in the treatment of cardiac arrest, e.g., to provide return of spontaneous circulation. Lastly, intravenous injection of this vasopressor provides critical care relief of hypotension associated with certain types of shock and fluid refractory shock, including septic shock, and relief of anaphylactic shock.

Although epinephrine has many uses, including many life saving uses, existing liquid formulations of epinephrine are associated with reduced potency, less desirable effects, or have the potential to cause harm. Formulations of epinephrine are plagued by two major problems, racemization and oxidation. Racemization is the enantiomeric conversion of l-epinephrine into its less biologically active dextrorotatory isoform, d-epinephrine, which has a significantly low pressor effect; about one-fifteenth that of l-epinephrine. The d-isoform may also affect adrenergic receptor subtypes differently than the l-isoform, resulting in substandard and undesirable effects. Because the United States Pharmacopeia, USP, monograph for epinephrine injection does not include specifications for d-epinephrine content, only total epinephrine content, manufacturers of epinephrine drug products are not required to test the chirality of their formulation and significant racemization occurs, thus leading to a less potent product with less desirable effects. In actuality, the d-epinephrine isoform should be classified as an impurity in an l-epinephrine drug product. It is believed that the epinephrine injection USP monograph does not include specifications for d-epinephrine because preventing its formation through racemization had proven too challenging. Whereas, oxidation of epinephrine can be prevented to a certain extent, including the use of antioxidants. The oxidation of epinephrine's alcohol group forms its less potent ketone form, known as adrenalone, which has little if any beta adrenergic activity. Racemization and oxidation of epinephrine are associated with reduced potency and less desirable effects as the impurities d-epinephrine and adrenalone form at the expense of l-epinephrine.

Drug manufacturers try to deal with the problem of oxidation by adding bisulfite antioxidants and increasing overages, both of which have the potential to cause harm to patients. Preservatives, such as sodium metabisulfite, are added to epinephrine formulations as antioxidants to reduce oxidation and to help keep formulations sterile. Sterilization techniques themselves often result in the loss of total epinephrine, and l-epinephrine, which may be compensated with increased overages. Sodium bisulfite and sodium metabisulfite, bisulfites, can cause mild to severe, life-threatening allergic reactions, including anaphylaxis or asthmatic episodes in susceptible individuals, especially those with sulfite sensitivities. So while epinephrine is indicated for treating anaphylaxis, the presence of sulfites in its formulation puts susceptible patients at great risk of exacerbating their anaphylaxis to the point of death. And for patients who are in other critical situations, such as cardiac arrest or septic shock, such sulfite reactions could greatly worsen the critical condition of these vulnerable patients. Most formulations also use overages of active pharmaceutical ingredient to compensate for degradation of epinephrine content and activity over the course of the product's shelf-life. This results in epinephrine drug products released after manufacturing with a higher than expected activity, which could be hazardous to patients as causing higher infusion and injection doses, thereby increasing side effects such as tachycardia.

In addition to the degradants d-epinephrine and adrenalone, which have been mentioned to have little pharmacological activity compared with l-epinephrine, lesser other degradants include adrenochrome and adrenolotin. A potentially toxic impurity, epinephrine sulfonate, forms by sulfonation reaction in epinephrine drug products containing sulfites.

Due to the deficiencies in existing pharmaceutical formulations of l-epinephrine, the identity, strength, quality, purity, and/or potency of the drug product cannot be adequately assured, or neither can its safety. There exists a great need for a liquid formulation of l-epinephrine that is preferably both preservative-free and sulfite-free, with minimal average, if any, and with minimal levels of degradants, including d-epinephrine, while maintaining a sterility guarantee There also exists a great need for prefilled syringes of l-epinephrine, to deliver greater dose than an autoinjector would and because the cost of epinephrine autoinjectors are excessively high and cost prohibitive to most patients and institutions. Currently, there are no prefilled syringes of l-epinephrine that have been approved for safety and efficacy by the Food and Drug Administration (FDA), and for instance, prefilled syringes of 1 mL of 1 mg per mL l-epinephrine are not even available for use as unapproved drug products. The present invention provides for prefilled syringes of an at least 1 mL or an at least 1 mg injectable liquid pharmaceutical formulation of epinephrine having high l-epinephrine content and also so that there are no issues of subpotency or harmful impurities with this more stable formulation.

Importantly, the present invention fulfills unmet medical need by providing methods of use, including treating patients with a prefilled syringe of l-epinephrine, in a unique way of injecting into an intravenous fluid bag for continuous intravenous infusion. Formerly, epinephrine from unapproved drug products was transferred with loss or degradation from an ampule or vial to an intravenous bag or injected as bolus administration without an intravenous bag to a patient. There is nothing obvious about using a prefilled syringe in the method of continuous intravenous administration when prefilled syringes currently administer bolus doses of drugs and would teach against continuous intravenous administration. Therefore, the present invention fulfills an unmet medical need of providing high potency, high purity l-epinephrine by continuous intravenous infusion for patients requiring hemodynamic support with nearly no loss or degradation of l-epinephrine; thereby, providing new safer methods of medicinal use to achieve an improved standard of patient care.

SUMMARY OF THE INVENTION

In one embodiment, the invention provides a method of treating a patient having, developing, or recovering from septic shock with a continuous intravenous infusion of l-epinephrine delivered via an at least one intravenous fluid bag with an at least one intravenous line and/or an at least one intravenous catheter, said at least one intravenous fluid bag containing up to 1,000 mL of a saline solution or a dextrose and sodium chloride-containing solution, said method comprising:

a) injecting an at least a portion of an at least one greater than 2 mL prefilled container of a 1 mg per mL injectable liquid pharmaceutical formulation of l-epinephrine into each said at least one intravenous fluid bag or medication port thereof, so that the at least one intravenous fluid bag has a diluted concentration of l-epinephrine of about 1 microgram per mL, wherein said at least one greater than 2 mL prefilled container injectable liquid pharmaceutical formulation of l-epinephrine comprises a tonicity agent and is free of epinephrine bitartrate ingredient;

b) said method further comprising administering said continuous intravenous infusion of l-epinephrine to said patient at said diluted concentration of l-epinephrine at about 1 microgram per mL;

c) said method further comprising titrating said continuous infusion of l-epinephrine based on a blood pressure of said patient to achieve the desired hemodynamic goals or to stabilize said patient's vital signs;

d) said method further comprising weaning said continuous infusion of l-epinephrine;

e) said method optionally comprising protecting said at least one said intravenous fluid bag from light or UV-radiation after said step of injecting said at least a portion of said at least one greater than 2 mL prefilled container into said at least one intravenous fluid bag or medication port thereof to prevent l-epinephrine degradation and impurities from forming so that said continuous intravenous infusion of l-epinephrine has a ratio of l-epinephrine:d-epinephrine greater than 4:1.

In one embodiment, the method results in increasing heart rate and heart contractility in the patient.

In one embodiment, the at least one intravenous fluid bag is at least two intravenous fluid bags.

In another embodiment, the step (b) is administered for at least half a day.

In another embodiment, the step (b) is administered for at least one day.

In another embodiment, each at least one greater than 2 mL prefilled container injectable liquid pharmaceutical formulation of l-epinephrine has no more than 12.5% total impurities or no more than 12% d-epinephrine.

In another embodiment, the at least one greater than 2 mL prefilled container of a 1 mg per mL injectable liquid pharmaceutical formulation of l-epinephrine is at least two greater than 2 mL prefilled container vials or bottles of a 1 mg per mL injectable liquid pharmaceutical formulation of l-epinephrine.

In another embodiment, the at least one greater than 2 mL prefilled container of a 1 mg per mL injectable liquid pharmaceutical formulation of l-epinephrine is a vial or bottle that contains at least 2.5 mL of a 1 mg per mL injectable liquid pharmaceutical formulation of l-epinephrine.

In another embodiment, the at least one greater than 2 mL prefilled container of a 1 mg per mL injectable liquid pharmaceutical formulation of l-epinephrine is a vial or bottle that contains at least 10 mL of a 1 mg per mL injectable liquid pharmaceutical formulation of l-epinephrine.

In another embodiment, the at least one greater than 2 mL prefilled container of a 1 mg per mL injectable liquid pharmaceutical formulation of l-epinephrine is a vial or bottle that contains at least 30 mL of a 1 mg per mL injectable liquid pharmaceutical formulation of l-epinephrine.

In another embodiment, the at least one greater than 2 mL prefilled container of a 1 mg per mL injectable liquid pharmaceutical formulation of l-epinephrine is a vial or bottle that contains multiple doses of l-epinephrine to prepare multiple intravenous fluid bags with a diluted concentration of l-epinephrine of about 1 microgram per mL in each intravenous fluid bag.

DETAILED DESCRIPTION OF THE INVENTION

Past solutions of epinephrine have included a microbial preservative in order to assure the sterility of the drug product, even if the drug product was a single-use vial used immediately after opening. Sulfites were able to counter the oxidative behavior of epinephrine by reacting with residual oxygen in its container instead of reacting with epinephrine, and thus, sequestered the free oxygen. When dissolution of the epinephrine was carried out by means of addition of diluted hydrochloric acid, HCl, some excess of acid could maintain a low pH near 2.2 and slow the degradation of epinephrine, also by forming inactive sulphonic acid.

Improved methods of preparation of sulfite-free pharmaceutical formulations of epinephrine included the compounding of the drug substance, followed by initial filtration, filling and sterilization. In order to produce and assure a sterile pharmaceutical solution of epinephrine as a drug product for injectable use, and without including preservatives such as metabisulfites, terminal heat sterilization following filling and/or final filtration under aseptic conditions during filling must be employed.

The compounding step utilized an active l-epinephrine pharmaceutical ingredient base, such as l-epinephrine hydrochloride, USP. This compounding step was performed to place the solid/powder active pharmaceutical ingredient into aqueous solution. Water for injection was the solvent. Mixing alone will not bring l-epinephrine into aqueous solution adequately. The pH of the solution must be lowered in order for the l-epinephrine base to dissolve properly. The pH can be lowered with an acid, such as an organic acid, and preferably 1 Normal (1N) hydrochloric acid that serves as a dissolution agent and a pH adjuster. Since the final solution will be injected into patients, the tonicity of the solution must be increased with a tonicity agent. Although various tonicity agents can be employed, the present methods preferably employ the use of sodium chloride as a tonicity agent. The batch formula per mL was 1.1 mg epinephrine base as the drug substance, 8.6 mg sodium chloride as the tonicity agent, 7.26 g hydrochloric acid (1N) as the dissolution agent, additional hydrochloric acid (1N) as a pH adjuster to lower pH to 2.2 to 2.6, and 987.04 mg water for injection as a solvent. Ideally, the compounding step and subsequent filtration step were conducted under inert nitrogen atmosphere to help prevent exposure of epinephrine and its solution to oxygen. It can be seen from this batch formula that a high 10% average of epinephrine base was used to compensate for degradation over time, when the desired final concentration is 1 mg/mL epinephrine.

The compounded solution of l-epinephrine was then filtered, such as by a 0.22 micrometer filter and transferred to a sterilized, preferably glass, vessel. Filtration of the compounded solution removed any particulates, whether bacterial or undissolved ingredients.

The filtered solution of epinephrine was then filled into sterilized or sterile containers using sterilized filling equipment. Sterile containers included, but were not limited to, glass ampules, glass vials with caps, glass bottles with caps, and syringes to make prefilled syringes or autoinjectors. To help protect the epinephrine solution against oxidation since no metabisulfites were used in the formulation, the filling step was performed under an inert atmosphere of nitrogen that is essentially devoid of oxygen to reduce the residual oxygen content in the empty space of the filled container. This filling step could be performed under aseptic conditions along with additional filtration, such as by a 0.22 micrometer filter integrated with the filling equipment. Alternatively, or additionally, filled containers could be sterilized by heat, such as by using an autoclave or by steam sterilization. Terminal sterilization at a temperature above the boiling point of water, such terminal sterilization at 121° C., with overkill conditions assured sterility guarantee of the final drug product. For example, a $F_o$ of 10 minutes by means of a steered sterilization cycle was initially chosen to reduce the thermal stress on the epinephrine solution. Because thermal stress was not found to degrade epinephrine, overkill conditions of sterilization could be used. Degradation of epinephrine was found mainly attributed to exposure to oxygen, which was directly related to nitrogen purge accuracy during the production and filling phases, instead of thermal treatment.

The above steps described the overall manufacturing process in making a drug product of preservative-free, sulfite-free solution of epinephrine. Specifically, it was found that this process inclusive of a 10% average and an in-process pH range of 2.2 to 2.6 produced an epinephrine solution that could support a shelf-life of a 2 mL glass ampule containing 1 mL epinephrine solution for at least 48 months when studied in a climatic chamber at 25° C. for a maximum storage time of 60 months, in a climatic chamber at 30° C. for a maximum storage time of 12 months, and in a climatic chamber at 40° C. for a maximum storage time of 6 months.

However, this drug product produced by this manufacturing process with an in-process pH of approximately 2.5 was found to be inferior, and not only because of its high 10% average. It was decided to test this epinephrine solution for d-epinephrine content even though there is no such rationale by USP or the industry to do so. When tested for d-epinephrine content by a chiral HPLC analytical method, it was unexpectedly found that approximately 14% of the l-epinephrine had been racemized into d-epinephrine at the product's release. After storage at 25° C. for 6 months, at least 19% of the l-epinephrine was converted to d-epinephrine. The drug product produced in this manner would contain less than 90% l-epinephrine in well under a year, and for all practical purposes, was unsuitable for use.

Producing an epinephrine drug product with a high l-epinephrine content, such as greater than 90%, throughout its shelf-life of over one year seemed impossible in a preservative-free, sulfite-free solution, and had never been accomplished before. Increasing overages above 10% was not a viable solution. Terminal sterilization of the epinephrine solution only contributed to about 4% racemization, so eliminating heat sterilization and depending solely on aseptic filtration would not solve the racemization problem, nor have as strong of a final sterility guarantee in this antimicrobial-free solution. Lowering the in-process pH was not believed possible due to oxidation issues. The lower the pH was to 2.2, the lower the impact was of potential oxygen residues in the solution. The thought of raising the in-process pH above the 2.2-2.6 of previous methods, and allowing for additional oxidation in an antioxidant-free solution, was contradictory to one skilled in the art.

Inadvertently, increasing the in-process pH to 2.8-3.3, unexpectedly reduced the racemization of l-epinephrine to d-epinephrine at release by approximately two-thirds, from 14% to 5%, respectively. To the contrary, these results led to the discovery that in a preservative-free, sulfite-free, l-epinephrine solution, racemization was a more significant problem than expected, even more so than oxidation. This discovery led to new methods of manufacturing sulfite-free, l-epinephrine solution with an in-process pH of 2.8 to 3.3, approximately 3.0, which was a nonobvious solution to the problem of racemization. Most importantly, with these new methods, overages could greatly be reduced.

The new method of preparing a 1 mg/mL solution of l-epinephrine, such as in a glass ampule, has a revised batch formula per mL of: approximately 1.03 mg epinephrine base, as the drug substance, 8.6 mg sodium chloride as the tonicity agent, 7.26 g hydrochloric acid (1N) as the dissolution agent, additional hydrochloric acid (1N) as a pH adjuster to lower pH only to 2.8 to 3.3, and 987.11 mg water for injection as a solvent. The compounding of the drug substance, followed by initial filtration, filling and sterilization are all conducted under inert nitrogen atmosphere to help prevent exposure of epinephrine and its solution to oxygen.

With less than or no more than a 6% average, and preferably a 3% average, a viable shelf-life of at least one year, e.g., at least 15 months, was achieved with the new method with more than 90% l-epinephrine content at the end of the shelf-life. A sealed 2 mL glass ampule served as the container for the 1 mL drug product that was tested. However, the drug product solution of the present invention can be made in larger volumes in other sterile containers, including glass vials and bottles, and syringes and autoinjectors; including autoinjectors conducive with the preservative-free formulation. The new and improved formulation with reduced average also has less than or no more than 6.5% total impurities, including less than or no more than 6% d-epinephrine and less than or no more than 0.5% adrenalone at release; and less than or no more than 12.5% total impurities, including less than or no more than 12% d-epinephrine and less than or no more than 0.5% adrenalone through a shelf-life of at least 12 months, and preferably through a shelf-life of at least 15 months. If aseptic filtration is used without terminal sterilization, these new methods would allow an l-epinephrine drug product to be prepared without any average of epinephrine base, so that exactly 1.00 mg of epinephrine base is used per mL in the compounding step.

These inventive methods have discovered and achieved new limits for an injectable liquid pharmaceutical formulation of l-epinephrine sterile solution; less than or no more than about 6% d-epinephrine at release, and less than or no more than about 12% d-epinephrine through a shelf-life of at least 12 months; which has never been accomplished before, even if preservatives/sulfites are optionally included in the formulation as alternate embodiments (e.g., preservatives/sulfites up to about 1 mg per mL, such as sodium metabisulfite). Although these injectable liquid pharmaceutical formulations of l-epinephrine sterile solution introduced by this invention can be produced having any desirable concentration of l-epinephrine, they are preferably compounded in an aqueous solution as approximately 1.0 to 1.06 mg/mL l-epinephrine, and further include a tonicity agent, and include no more than about 6% d-epinephrine and no more than about 0.5% adrenalone at release, and no more than about 12% d-epinephrine and no more than about 0.5% adrenalone over a shelf-life of at least 12 months. Such injectable liquid pharmaceutical formulations of l-epinephrine sterile solution taught by this invention have uncompromised potency of l-epinephrine at release and through their shelf-life.

The present invention therefore provides improved methods of formulating safer and more reliable pharmaceutical preparations of epinephrine for medicinal use. Unlike other epinephrine formulations, these improved formulations are preservative-free and sulfite-free so that there are no safety issues for anaphylaxis and no toxic epinephrine sulfonate byproducts. These improved epinephrine formulations have no need for high overages, and use minimal overages, if any to assure reliable dosage. The present methods of this invention preferably use l-epinephrine hydrochloride, USP as the active pharmaceutical ingredient base, although other l-epinephrine active ingredients and salts and combinations thereof can be employed, including epinephrine bitartrate. The present methods of this invention preferably use sterile containers including, but not limited to, glass ampules, glass vials with caps, glass bottles with caps, and syringes to make prefilled syringes or autoinjectors. Other inert gases, instead of or in addition to nitrogen, can be used for the manufacturing process. Other concentrations of sulfite-free, l-epinephrine solution greater or lower than approximately 1 mg/mL can also be prepared using these new methods and in-process pH under nitrogen (inert gas) atmosphere, where nitrogen (inert gas) purge accuracy is inversely related to oxygen exposure during the production and filling phases.

The present invention also includes methods of using these more potent and less toxic liquid formulations of l-epinephrine as eye drops to provide mydriasis during intraocular surgery; as a solution for nebulization to provide bronchodilation and relief of bronchospasm to asthmatics and those with chronic obstructive pulmonary disease; as a solution combined with analgesics for injection, including lidocaine for dental applications and tumescent anesthesia and tumescent liposuction; and bupivacaine for epidural analgesia, to improve and lengthen pain relief and sensory blockade during surgical procedures; as a solution for intramuscular or subcutaneous injection to counter symptoms associated with anaphylaxis or to help stop bleeding associated with peptic ulcers and surgical procedures; as a solution for intravenous injection in the treatment of cardiac arrest, to provide return of spontaneous circulation; and as a solution for intravenous injection to relieve hypotension associated with certain types of shock and fluid refractory shock, including septic shock.

Anaphylaxis is a severe allergic reaction with rapid onset that can result in death. Symptoms include rash, swelling in the throat or tongue, shortness of breath, vomiting, dizziness, and importantly, low blood pressure. Severe or untreated anaphylaxis can lead to anaphylactic shock, a state in which the drop in blood pressure causes inadequate blood perfusion to tissues, resulting in cellular and tissue damage and organ failure that can lead to death. The trigger for anaphylaxis can be exposure to a certain food or drug, an insect sting, or can be brought on by exercise. Other times, the cause of anaphylaxis is unknown; is idiopathic.

The primary treatment for anaphylaxis is injection of epinephrine, by bolus intravenous, intramuscular, or subcutaneous injection. With both alpha- and beta-adrenergic effects, epinephrine serves as a vasotropic agent that constricts blood vessels to offset the vasodilation brought on by anaphylaxis so as to restore adequate blood pressure. Epinephrine also serves as an inotropic agent that increases heart rate. Epinephrine's beta-adrenergic effects relieve difficulty in breathing by relaxing bronchial tissue in the lungs as a bronchodilator. Epinephrine may also alleviate itching, swelling, and tissue edema.

Autoinjectors have made intramuscular and subcutaneous injection of epinephrine easier and more convenient to patients as such epinephrine injections can be self-administered and portable for travel.

Sulfites (e.g., sodium bisulfite, sodium metabisulfite, sodium sulfite, potassium bisulfite, and potassium metabisulfite) are chemicals added to foods and drugs as an anti-oxidant or preservative. Interestingly, the symptoms of anaphylaxis mirror those of sulfite-sensitivity or sulfite-allergy: bronchoconstriction, hypotension, dyspnea, urticaria, laryngeal edema, itching and swelling, and even shock. Sometimes a patient can be known to be sulfite-sensitive or sulfite-allergic. Other times, sulfite-sensitivity or sulfite-allergy can happen in a patient not known to be sulfite-sensitive or sulfite-allergic. It is thought that asthmatics generally have a higher predisposition sulfite-sensitivity or sulfite-allergy. Studies have demonstrated that sulfites may cause allergic-type reactions in certain susceptible persons, especially asthmatics. The term sulfite-sensitivity is sometimes used interchangeably with sulfite-allergy, but is more correctly used instead of sulfite-allergy when immunoglobulins to sulfites have not been detected. There are many theories to the mechanism of sulfite-sensitivity. Regardless of which theory proves true, individuals have died from eating at salad bars due to foods being sprayed with sulfites. Medications containing sulfites also place some patients at great risk.

The FDA requires a sulfite warning in the label of sulfite-containing prescription drug products, which also mentions the uncertainty of who may have sulfite-allergy. The prescription drug label must mention which sulfite it contains, a sulfite that may cause allergic-type reactions including anaphylactic symptoms and life-threatening or less severe asthmatic episodes in certain susceptible people.

Ironically, current autoinjectors of epinephrine on the market to treat anaphylaxis contain sulfites. If the patient turns out to have a sulfite-sensitivity or sulfite-allergy, the anaphylactic symptoms may decrease from the epinephrine, then suddenly reappear from reaction to sulfites in the formulation. This may result in a prolonged cycle of extra epinephrine injections, because the sulfites may cause or exacerbate the anaphylaxis, making the anaphylaxis more severe or life-threatening. The time between recurrence of symptoms may give a false sense of security as patients may believe the sulfite-containing epinephrine autoinjector cured their anaphylaxis, only to have anaphylaxis return from sulfite-sensitivity an hour or so later. During this window, the patient may be away from a hospital or be without additional autoinjectors, and therefore, be in danger when symptoms re-occur and their airways constrict.

Because there had not been any sulfite-free, epinephrine drug products approved by the FDA, physicians and patients were left without safer alternatives, because an alternative to using epinephrine in a life-threatening situation may not be satisfactory. Fortunately, the preservative-free and sulfite-free formulation of the present invention has been FDA approved, which is believed to provide a safer alternative in patients with known or unknown sulfite-sensitivity, and can be supplied in autoinjector form.

The present invention is a method of treating allergic reaction, anaphylaxis, anaphylactic shock, or a combination thereof by an injection of at least one dosage of an injectable liquid pharmaceutical formulation of preservative-free and sulfite-free l-epinephrine sterile solution. The injectable liquid pharmaceutical formulation is compounded in an aqueous solution as approximately 1.0 to 1.06 mg/mL l-epinephrine, and further includes a tonicity agent. The injectable liquid pharmaceutical formulation has a pH between 2.8 and 3.3. The liquid pharmaceutical formulation includes no more than about 6% d-epinephrine and no more than about 0.5% adrenalone at release, and no more than about 12% d-epinephrine and no more than about 0.5% adrenalone over a shelf-life of at least 12 months.

The injectable liquid pharmaceutical formulation is compounded in an aqueous solution preferably as 1.03 mg/mL l-epinephrine.

The injectable liquid pharmaceutical formulation preferably has a concentration of 1 mg per mL l-epinephrine.

The injectable liquid pharmaceutical formulation can be stored in a container with an inert gas prior to use.

The injection is preferably intramuscular or subcutaneous injection and is preferably administered by an autoinjector containing the injectable liquid pharmaceutical formulation.

The at least one dosage of an injectable liquid pharmaceutical formulation of preservative-free and sulfite-free, 1 mg per mL l-epinephrine sterile solution is preferably and approximately 0.30 mg l-epinephrine.

Alternatively, such as for pediatric patients, the at least one dosage of an injectable liquid pharmaceutical formulation of preservative-free and sulfite-free, 1 mg per mL l-epinephrine sterile solution is approximately 0.15 mg l-epinephrine.

For more severe cases, the at least one dosage of an injectable liquid pharmaceutical formulation of preservative-free and sulfite-free, 1 mg per mL l-epinephrine sterile solution can be approximately 0.50 mg l-epinephrine.

Importantly, the method of treating allergic reaction, anaphylaxis, anaphylactic shock, or a combination thereof is also performed in patients with known or unknown sulfite-sensitivity or sulfite-allergy. This method further prevents the exacerbation, extension, or recurrence of allergic reaction, anaphylaxis, anaphylactic shock, or a combination thereof caused by sulfite-sensitivity or sulfite-allergy by avoiding additional sulfite-exposure. Such additional sulfite-exposure which would otherwise come from sulfite-containing epinephrine products and autoinjectors.

In another method embodiment, the method is for treating allergic reaction, anaphylaxis, anaphylactic shock, or a combination thereof in a patient with known or unknown sulfite-sensitivity or sulfite-allergy by an intramuscular or subcutaneous injection of at least one 0.15 mg to 0.50 mg l-epinephrine dosage of an injectable liquid pharmaceutical formulation of preservative-free and sulfite-free, 1 mg per mL l-epinephrine sterile solution administered by an autoinjector containing the at least one dosage of the injectable liquid pharmaceutical formulation. The injectable liquid pharmaceutical formulation is compounded in an aqueous solution as approximately 1.0 to 1.06 mg/mL l-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months.

The injectable liquid pharmaceutical formulation can be stored in a container with an inert gas prior to use.

The injectable liquid pharmaceutical formulation preferably has no more than 12.5% total impurities over a shelf-life of at least 15 months, including no more than 12% d-epinephrine and no more than 0.5% adrenalone.

The method can be applied specifically to patients whose anaphylaxis was triggered by sulfite exposure from other medications. The method of treating allergic reaction, anaphylaxis, anaphylactic shock, or a combination thereof that is caused by or exacerbated by sulfite exposure from sulfite-containing medications in a patient with known or unknown sulfite-sensitivity or sulfite-allergy; the method including an intramuscular or subcutaneous injection of at least one 0.15 mg to 0.50 mg l-epinephrine dosage of an injectable liquid pharmaceutical formulation of preservative-free and sulfite-free, 1 mg per mL l-epinephrine sterile solution administered by an autoinjector containing the at least one dosage of the injectable liquid pharmaceutical formulation. The injectable liquid pharmaceutical formulation is compounded in an aqueous solution as approximately 1.0 to 1.06 mg/mL l-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months.

The method can also be applied specifically to patients whose anaphylaxis was triggered by sulfite exposure from a sulfite-containing autoinjector of epinephrine. The method of treating allergic reaction, anaphylaxis, anaphylactic shock, or a combination thereof that is caused by or exacerbated by sulfite exposure from a sulfite-containing epinephrine formulation administered by an autoinjector in a patient with known or unknown sulfite-sensitivity or sulfite-allergy; the method including an intramuscular or subcutaneous injection of at least one 0.15 mg to 0.50 mg l-epinephrine dosage of an injectable liquid pharmaceutical formulation of preservative-free and sulfite-free, 1 mg per mL l-epinephrine sterile solution administered by an autoinjector containing the at least one dosage of the injectable liquid pharmaceutical formulation. The injectable liquid pharmaceutical formulation is compounded in an aqueous solution as approximately 1.0 to 1.06 mg/mL l-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months.

The invention is also, therefore, an autoinjector containing at least one 0.15 mg to 0.50 mg l-epinephrine dosage of an injectable liquid pharmaceutical formulation of preservative-free and sulfite-free, 1 mg per mL l-epinephrine sterile solution. The injectable liquid pharmaceutical formulation is compounded in an aqueous solution as approximately 1.0 to 1.06 mg/mL l-epinephrine, and further includes a tonicity agent. The injectable liquid pharmaceutical formulation has a pH between 2.8 and 3.3. The liquid pharmaceutical formulation has no more than 6.5% total impurities at release, and no more than 12.5% total impurities over a shelf-life of at least 12 months. The autoinjector of the present invention is used for treating allergic reaction, anaphylaxis, anaphylactic shock, or a combination thereof in a patient with known or unknown sulfite-sensitivity or sulfite-allergy by providing an intramuscular or subcutaneous injection of the injectable liquid pharmaceutical formulation to the patient.

There also exists a great need for prefilled syringes of l-epinephrine, to deliver greater dose than an autoinjector would and because the cost of epinephrine autoinjectors are excessively high and cost prohibitive to most patients and institutions. Currently, there are no prefilled syringes of l-epinephrine approved for safety and efficacy by the Food and Drug Administration (FDA), and for instance, prefilled syringes of 1 mL of 1 mg per mL l-epinephrine are not even available for use as unapproved drug products. The present invention provides for prefilled syringes of an at least 1 mL or 1 mg injectable liquid pharmaceutical formulation of epinephrine having high l-epinephrine content and also so that there are no issues of subpotency or harmful impurities.

Importantly, the present invention fulfills unmet medical need by providing methods of use, including treating patients with a syringe or prefilled syringe of l-epinephrine, in a unique way of injecting into an intravenous fluid bag for continuous intravenous infusion. Formerly, epinephrine from unapproved drug products was transferred with loss or degradation from an ampule or vial to an intravenous bag or injected as bolus administration without an intravenous bag to a patient. There is nothing obvious about using a prefilled syringe in the method of continuous intravenous administration when prefilled syringes currently administer bolus doses of drugs and would teach against continuous intravenous administration. Therefore, the present invention fulfills an unmet medical need of providing high potency, high purity l-epinephrine by continuous intravenous infusion for patients requiring hemodynamic support with nearly no loss or degradation of l-epinephrine; thereby, providing new safer methods of medicinal use to achieve an improved standard of patient care.

The present invention include a method of performing vasoconstriction and increasing perfusion or raising a blood pressure in a patient with a continuous intravenous infusion of epinephrine delivered via an intravenous fluid bag with an intravenous line and or an intravenous catheter. Generally, intravenous lines are connected to an intravenous catheter, the standard of infusion care; however, certain emergency situations may connect an intravenous line directly to a needle or butterfly needle for administration into a vein. Importantly, this method comprises the step of injecting a prefilled syringe of an at least 1 mL or 1 mg injectable liquid pharmaceutical formulation of epinephrine into this intravenous fluid bag or a medication port of this intravenous fluid bag. This method further comprises the diluting of epinephrine to a concentration less than 1 mg per 100 mL in this intravenous fluid bag during this continuous intravenous infusion of epinephrine. The method also or alternatively comprises increasing heart contraction and heart rate of the patient. The raising of a blood pressure in the patient is at least mean arterial pressure. The intravenous fluid bag initially contains a premixed saline solution of 50 mL to about 1000 mL. Usually this is 0.9% normal saline, sodium chloride solution. Ideally, the intravenous fluid bag initially contains a sugar and saline solution of 50 mL to about 1000 mL, and preferably this intravenous fluid bag initially contains 1000 mL of a premixed 5 percent dextrose and 0.9% sodium chloride-containing solution. The dextrose or sugar in the intravenous fluid bag helps prevent oxidation and or racemization of l-epinephrine.

The at least one syringe or prefilled syringe of an at least 1 mL or 1 mg injectable liquid pharmaceutical formulation of epinephrine will either have a luer fitting or luer lock syringe tip that can insert into a medication port of the intravenous fluid bag or accept a needle that can be injected through the bag material or into the medication port of the intravenous fluid bag. Alternatively, the at least one syringe or prefilled syringe of an at least 1 mL or 1 mg injectable liquid pharmaceutical formulation of epinephrine is a staked needle syringe that can be injected through the bag material or into the medication port of the intravenous fluid bag. The at least one syringe or prefilled syringe of an at least 1 mL or 1 mg injectable liquid pharmaceutical formulation of epinephrine may be a standard glass, plastic, and or crystal zenith syringe that is manually injected, or may contain a vial or cartridge component.

The at least one syringe or prefilled syringe of an at least 1 mL or 1 mg injectable liquid pharmaceutical formulation of epinephrine preferably contains 1 mL of a 1 mg per mL concentration of epinephrine, such as may be of a glass l mL Long glass syringe. In other embodiments, the at least one syringe or prefilled syringe of an at least 1 mL or 1 mg injectable liquid pharmaceutical formulation of epinephrine preferably contains 10 mL of a 0.1 mg per mL concentration of epinephrine.

The at least one syringe or prefilled syringe of an at least 1 mL or 1 mg injectable liquid pharmaceutical formulation of epinephrine further has a ratio of l-epinehrine:d-epinephrine greater than about 6:1 and preferably at least 9:1. When said at least one syringe or prefilled syringe of an at least 1 mL or 1 mg injectable liquid pharmaceutical formulation of epinephrine is injected into the at least one intravenous fluid bag, the ratio of ratio of l-epinephrine:d-epinephrine in the intravenous fluid bag and or the continuous intravenous infusion is much greater than 4:1, even greater than about 6:1, and preferably is at least 9:1. Because of sulfite-sensitivity, which is usually unknown to most patients, the at least one syringe or prefilled syringe of an at least 1 mL or 1 mg injectable liquid pharmaceutical formulation of epinephrine is preferably preservative-free and or sulfite-free; which is technically challenging to maintaining the high l-epinephrine:d-epinephrine ratio since oxidation and racemization would otherwise occur.

In some instances, the at least one container or prefilled syringe of an at least 1 mL or 1 mg injectable liquid pharmaceutical formulation of epinephrine is terminally heat sterilized. But it was uniquely found that terminal heat sterilization can be avoided under certain conditions if no terminal sterilization is used, or if irradiating sterilization, such as gamma-sterilization, or ethylene oxide sterilization is used and compatible with certain syringe components.

Importantly, the invention also includes methods of producing and using these pharmaceutical formulations of l-epinephrine, including preventing and or treating hypotension and hemostasis under surgical anesthesia.

The invention is a method of treating hypotension in a patient having or recovering from invasive orthopedic or gynecological procedures, surgery, or a combination thereof. These types of invasive orthopedic or gynecological procedures or surgery can include, but are not limited to, knee replacement surgery, hip replacement surgery, hysterectomy, and even procedures of or during child birth or cesarean section. Such hypotension can be the result of the invasive procedure or surgery itself, such as but not limited to bleeding, and or, a side effect of one or more anesthetic agents. Anesthetic agents can include, but are not limited to, amide anesthetics such as lidocaine, prilocaine, bupivicaine, chloroprocaine; barbiturates; benzodiazepines; ketamine; propofol; and many others. The method includes a continuous intravenous infusion of l-epinephrine delivered via an at least one intravenous fluid bag with an at least one intravenous line and or an at least one intravenous catheter following a step of injecting said patient with an at least 1 microgram per mL solution of l-epinephrine in saline and or anesthetic into a subarachnoid space, epidural space, or a combination thereof to prolong anesthesia. The at least one intravenous fluid bag contains up to 1,000 mL of a dextrose and or saline-containing solution. The method comprises the step of injecting an at least one syringe of a 1 mg injectable liquid pharmaceutical formulation of l-epinephrine into each said at least one intravenous fluid bag or medication port thereof; this at least one syringe of a 1 mg injectable liquid pharmaceutical formulation of l-epinephrine includes a tonicity agent and has no more than 12.5% total impurities or no more than 12% d-epinephrine. The method further comprises the diluting of l-epinephrine to a concentration of about 1 microgram per mL in each said at least one said intravenous fluid bag during said continuous intravenous infusion of l-epinephrine. The method optionally comprises protecting the at least one said intravenous fluid bag from light or UV-radiation after said step of injecting said syringe into said at least one intravenous fluid bag or medication port thereof to prevent l-epinephrine degradation and impurities from forming so that the continuous intravenous infusion of l-epinephrine has a ratio of l-epinephrine:d-epinephrine greater than 4:1 to treat hypotension effectively.

The invention also is a method of preventing and or treating cardiac arrhythmias and hypotension in a patient having or recovering from invasive orthopedic or gynecological procedures, surgery, or a combination thereof. A unique situation exists when a patient undergoes surgery under general anesthesia (e.g., by inhalation) with general anesthetic agents containing halogenated hydrocarbons (e.g., halothane, desflurane) or cyclopropane. If such anesthetic agents are used, and the patient experiences hypotension as a result of the surgery itself and or as a side effect to the general anesthetic, then epinephrine cannot be used to treat the hypotension because these agents can sensitize the heart to epinephrine. Therefore, the method includes a step of replacing general anesthesia with regional anesthesia, so that pain can be treated, but without the general anesthetic agents. The method further including a step of injecting the patient with an at least 1 microgram per mL of l-epinephrine in anesthetic solution into a subarachnoid space, epidural space, or a combination thereof to treat or prevent pain. The at least 1 microgram per mL of l-epinephrine in anesthetic solution is prepared just prior to said step of injecting into said subarachnoid space, epidural space, or a combination thereof by mixing at least some of a 1 mg injectable liquid pharmaceutical formulation of l-epinephrine including a tonicity agent and having no more than 12.5% total impurities or no more than 12% d-epinephrine with at least some of an anesthetic solution. The method further includes a step of providing the patient with a continuous intravenous infusion of l-epinephrine delivered via an at least one intravenous fluid bag with an at least one intravenous line and or an at least one intravenous catheter; the at least one intravenous fluid bag containing up to 1,000 mL of a dextrose and or saline-containing solution; the method comprising the step of injecting an at least one syringe of a 1 mg injectable liquid pharmaceutical formulation of l-epinephrine into each said at least one intravenous fluid bag or medication port thereof; said at least one syringe of a 1 mg injectable liquid pharmaceutical formulation of l-epinephrine including a tonicity agent and having no more than 12.5% total impurities or no more than 12% d-epinephrine. The method further comprises the diluting of l-epinephrine to a concentration of about 1 microgram per mL in each said at least one said intravenous fluid bag during said continuous intravenous infusion of l-epinephrine. The method optionally comprises protecting the at least one said intravenous fluid bag from light or UV-radiation after said step of injecting said syringe into said at least one intravenous fluid bag or medication port thereof to prevent l-epinephrine degradation and impurities from forming so that said continuous intravenous infusion of l-epinephrine has a ratio of l-epinephrine:d-epinephrine greater than 4:1.

The invention is also a method of providing hemostasis to a patient while having invasive orthopedic or gynecological surgery, or a combination thereof. The method includes a step of injecting said patient with an at least 1 microgram per mL of l-epinephrine in anesthetic solution into a subarachnoid space, epidural space, or a combination thereof to treat or prevent pain during said invasive orthopedic or gynecological surgery. The at least 1 microgram per mL of l-epinephrine in anesthetic solution is prepared just prior to said step of injecting into said subarachnoid space, epidural space, or a combination thereof by mixing at least some of a 1 mg injectable liquid pharmaceutical formulation of l-epinephrine from an ampoule, syringe or prefilled syringe including a tonicity agent and having no more than 12.5% total impurities or no more than 12% d-epinephrine with at least some of an anesthetic solution. The method further includes a step of applying at least some of a 1 mg injectable liquid pharmaceutical formulation of l-epinephrine to bleeding tissue from an ampoule, syringe or prefilled syringe and optionally applied using a sponge, clothe, or pad; the 1 mg injectable liquid pharmaceutical formulation of l-epinephrine including a tonicity agent and having no more than 12.5% total impurities or no more than 12% d-epinephrine. This method stops or reduces surgical bleeding to the tissues.

The method optionally comprises protecting the at least one said intravenous fluid bag from light or UV-radiation after the step of injecting the prefilled syringe into the at least one intravenous fluid bag or medication port thereof to prevent epinephrine degradation and impurities from forming. A tinted and or opaque intravenous fluid bag is one unique option, but may be less desirable if the fluid cannot be checked for cloudiness or particulate matter, which can be harmful. Preferably, the method includes the step of covering at least one intravenous fluid bag with a light or UV-shielding material or clothe or bag to protect from exposure to light which could reduce the l-epinephrine:d-epinephrine ratio and or increase impurity levels.

The method further comprises the diluting of epinephrine to a concentration less than 1 mg per 100 mL in this intravenous fluid bag during this continuous intravenous infusion of epinephrine to an ideal concentration of about 1 microgram per mL epinephrine.

The continuous intravenous infusion of epinephrine of this method is at an infusion rate of at least 0.04 micrograms of epinephrine per kg body weight per min and less than 3 micrograms of epinephrine per kg body weight per min, at one or more time points during this continuous intravenous infusion. The continuous intravenous infusion of epinephrine is at an infusion rate that is titrated up or clown based on a the blood pressure of the patient to achieve the desired hemodynamic goals or to stabilize the patient's vital signs. The continuous intravenous infusion of epinephrine has an infusion rate that is incrementally adjusted by not more than 0.3 micrograms of epinephrine per kg body weight per min at a time so as to not overshoot desired hemodyamic or vital sign goals and or harm the patient.

In some instances, continuous intravenous infusion of epinephrine is maintained for at least half a day. In some instances, continuous intravenous infusion of epinephrine is weaned for at least half a day. For instance, treating a patient for septic shock may require a very long period of continuous intravenous infusion of epinephrine that could last more than one day. As such, this method provides for using multiple intravenous fluid bags injected with prefilled epinephrine syringes, sequentially. It can be envisioned in some circumstances, that multiple continuous intravenous infusions of epinephrine are needed with multiple intravenous fluid bags injected with prefilled epinephrine syringes simultaneously, as might be the case if a patient has circulatory blockages. The method allows for continuous intravenous infusion of epinephrine using more than one said intravenous fluid bag and more than one said prefilled syringe of an at least 1 mL or 1 mg injectable liquid pharmaceutical formulation of epinephrine.

The patient treated with this method is selected from patients having, developing, or recovering from a form of shock, septic shock, anaphylactic shock, myocardial infarction, or cardiac arrest; and or undergoing surgery.

A primary embodiment of the invention is a method of treating a patient having, developing, or recovering from a form of shock with a continuous intravenous infusion of epinephrine delivered via an at least one intravenous fluid bag with an at least one intravenous line and or an at least one intravenous catheter. The at least one intravenous fluid bag contains up to 1,000 mL of a dextrose and or saline-containing solution. The method comprises the step of injecting an at least one prefilled syringe of a 1 mg injectable liquid pharmaceutical formulation of epinephrine into each said at least one intravenous fluid bag or medication port thereof. The method further comprises the diluting of epinephrine to a concentration of about 1 microgram per mL in each at least one said intravenous fluid bag during the continuous intravenous infusion of epinephrine. The method optionally comprises protecting the at least one said intravenous fluid bag from light or UV-radiation after the step of injecting the prefilled syringe into the at least one intravenous fluid bag or medication port thereof to prevent epinephrine degradation and impurities from forming.

Another embodiment of the invention is a method of treating a patient having, developing, or recovering from septic shock or anaphylactic shock with a continuous intravenous infusion of epinephrine delivered via an at least one intravenous fluid bag with an at least one intravenous line and an at least one intravenous catheter. The at least one intravenous fluid bag contains up to 1,000 mL of a dextrose and or saline-containing solution, preferably 5 percent dextrose in 0.9 percent normal sodium chloride solution. The method comprises the step of injecting an at least one prefilled syringe of an at least 1 mL injectable liquid pharmaceutical formulation of epinephrine into each at least one intravenous fluid bag or medication port thereof. The method further comprising the diluting of epinephrine to a concentration of about 1 microgram per mL in each at least one intravenous fluid bag during said continuous intravenous infusion of epinephrine. The method optionally comprises protecting the at least one said intravenous fluid bag from light or UV-radiation after the step of injecting the prefilled syringe into the at least one intravenous fluid bag or medication port thereof to prevent epinephrine degradation and impurities from forming. The at least one intravenous fluid bag after injecting with the epinephrine prefilled syringe, and or the continuous intravenous infusion of epinephrine, have a ratio of l-epinehrine:d-epinephrine greater than 4:1 and preferably at least 9:1.

Another embodiment of the invention is a method of treating a patient having, developing, or recovering from septic shock or anaphylactic shock with a continuous intravenous infusion of epinephrine delivered via an at least one intravenous fluid bag with an at least one intravenous line and an at least one intravenous catheter. The at least one intravenous fluid bag contains up to 1,000 mL of a dextrose and or saline-containing solution. The method comprises the step of injecting an at least one prefilled syringe of a 1 mg in 10 mL injectable liquid pharmaceutical formulation of epinephrine into each said at least one intravenous fluid bag or medication port thereof. The method further comprises the diluting of epinephrine to a concentration of about 1 microgram per mL in each at least one intravenous fluid bag during said continuous intravenous infusion of epinephrine. The method optionally comprises protecting the at least one said intravenous fluid bag from light or UV-radiation after the step of injecting the prefilled syringe into the at least one intravenous fluid bag or medication port thereof to prevent epinephrine degradation and impurities from forming. The at least one intravenous fluid bag after injecting with the epinephrine prefilled syringe, and or the continuous intravenous infusion of epinephrine, have a ratio of l-epinehrine:d-epinephrine greater than 4:1 and preferably at least 9:1.

Other variations and embodiments of the invention described herein will now be apparent to those of skill in the art without departing from the disclosure of the invention or the coverage of the claims to follow.

What is claimed is:

1. A method of treating a patient having, developing, or recovering from septic shock with a continuous intravenous infusion of l-epinephrine delivered via an at least one intravenous fluid bag with an at least one intravenous line and/or an at least one intravenous catheter, said at least one intravenous fluid bag containing up to 1,000 mL of a saline solution or a dextrose and sodium chloride-containing solution, said method comprising:
   a) injecting an at least a portion of an at least one greater than 2 mL prefilled container of a 1 mg per mL injectable liquid pharmaceutical formulation of l-epinephrine into each said at least one intravenous fluid bag or medication port thereof, so that the at least one intravenous fluid bag has a diluted concentration of l-epinephrine of about 1 microgram per mL, wherein said at least one greater than 2 mL prefilled container injectable liquid pharmaceutical formulation of l-epinephrine comprises a tonicity agent and is free of epinephrine bitartrate ingredient;
   b) said method further comprising administering said continuous intravenous infusion of l-epinephrine to said patient at said diluted concentration of l-epinephrine at about 1 microgram per mL;
   c) said method further comprising titrating said continuous infusion of l-epinephrine based on a blood pressure of said patient to achieve the desired hemodynamic goals or to stabilize said patient's vital signs;
   d) said method further comprising weaning said continuous infusion of l-epinephrine;
   e) said method optionally comprising protecting said at least one said intravenous fluid bag from light or UV-radiation after said step of injecting said at least a portion of said at least one greater than 2 mL prefilled container into said at least one intravenous fluid bag or medication port thereof to prevent l-epinephrine degradation and impurities from forming so that said continuous intravenous infusion of l-epinephrine has a ratio of l-epinephrine:d-epinephrine greater than 4:1.

2. The method of claim 1, wherein the method results in increasing heart rate and heart contractility in the patient.

3. The method of claim 1, wherein the at least one intravenous fluid bag is at least two intravenous fluid bags.

4. The method of claim 1, wherein the step (b) is administered for at least half a day.

5. The method of claim 1, wherein the step (b) is administered for at least one day.

6. The method of claim 1, wherein each at least one greater than 2 mL prefilled container injectable liquid pharmaceutical formulation of l-epinephrine has no more than 12.5% total impurities or no more than 12% d-epinephrine.

7. The method of claim 1, wherein the at least one greater than 2 mL prefilled container of a 1 mg per mL injectable liquid pharmaceutical formulation of l-epinephrine is at least two greater than 2 mL prefilled container vials or bottles of a 1 mg per mL injectable liquid pharmaceutical formulation of l-epinephrine.

8. The method of claim 1, wherein the at least one greater than 2 mL prefilled container of a 1 mg per mL injectable liquid pharmaceutical formulation of l-epinephrine is a vial or bottle that contains at least 2.5 mL of a 1 mg per mL injectable liquid pharmaceutical formulation of l-epinephrine.

9. The method of claim 1, wherein the at least one greater than 2 mL prefilled container of a 1 mg per mL injectable liquid pharmaceutical formulation of l-epinephrine is a vial or bottle that contains at least 10 mL of a 1 mg per mL injectable liquid pharmaceutical formulation of l-epinephrine.

10. The method of claim 1, wherein the at least one greater than 2 mL prefilled container of a 1 mg per mL injectable liquid pharmaceutical formulation of l-epinephrine is a vial or bottle that contains at least 30 mL of a 1 mg per mL injectable liquid pharmaceutical formulation of l-epinephrine.

11. The method of claim 1, wherein the at least one greater than 2 mL prefilled container of a 1 mg per mL injectable liquid pharmaceutical formulation of l-epinephrine is a vial or bottle that contains multiple doses of l-epinephrine to prepare multiple intravenous fluid bags with a diluted concentration of l-epinephrine of about 1 microgram per mL in each intravenous fluid bag.

* * * * *